United States Patent
Huang et al.

(10) Patent No.: US 10,266,435 B2
(45) Date of Patent: Apr. 23, 2019

(54) COMPOSITE MATERIAL, METHOD AND DEVICE FOR PREPARING PARTICLE-ENERGY MULTIFUNCTIONAL ACTIVE WATER

(71) Applicant: JINGHUAN PARTICLE ENERGY TECHNOLOGY DEVELOPMENT CO., LTD., Beijing (CN)

(72) Inventors: Jinghuan Huang, Beijing (CN); Yaoquan Huang, Beijing (CN)

(73) Assignee: JINGHUAN PARTICLE ENERGY TECHNOLOGY DEVELOPMENT CO., LTD., Beijing (CN)

( * ) Notice: Subject to any disclaimer, the term of this patent is extended or adjusted under 35 U.S.C. 154(b) by 0 days.

(21) Appl. No.: 15/545,666

(22) PCT Filed: May 12, 2015

(86) PCT No.: PCT/CN2015/078758
§ 371 (c)(1),
(2) Date: Jul. 21, 2017

(87) PCT Pub. No.: WO2016/179792
PCT Pub. Date: Nov. 17, 2016

(65) Prior Publication Data
US 2018/0016167 A1    Jan. 18, 2018

(51) Int. Cl.
*C02F 1/68* (2006.01)
*A61K 33/00* (2006.01)
(Continued)

(52) U.S. Cl.
CPC ............... *C02F 1/68* (2013.01); *A23L 2/38* (2013.01); *A61K 33/00* (2013.01); *C02F 1/005* (2013.01);
(Continued)

(58) Field of Classification Search
CPC .. C02F 1/001; C02F 1/005; C02F 1/02; C02F 1/04; C02F 1/281; C02F 1/68; A61K 33/04; A61K 33/06; A61K 33/14
See application file for complete search history.

(56) References Cited

U.S. PATENT DOCUMENTS 4,569,823 A * 2/1986 Westin ............... B22F 1/0014
                                                        419/23
5,711,950 A    1/1998 Lorenzen
(Continued)

FOREIGN PATENT DOCUMENTS

CN         1868900 A    11/2006
CN      201136827 Y    10/2008
(Continued)

OTHER PUBLICATIONS

Machine translation of CN101684017A, publication date Mar. 31, 2010.*
(Continued)

*Primary Examiner* — Jun Li
(74) *Attorney, Agent, or Firm* — Maschoff Brennan

(57) ABSTRACT

A composite material, method and device for preparing particle-energy multifunctional active water. The composite material contains Si, Re, Pt, Ge, Nb, Ni, Se and Mg, and is prepared from nanometer-sized particles of these elements by magnetization, sintering and remagnetization. The composite material contacts and interacts with water to convert the water into the particle-energy multifunctional active water. The particle-energy multifunctional active water is smaller than small molecule group water, with specific gravity at normal temperature of 1.002-1.004 g/cm$^3$. The water is sterile, with stability and activity better than small molecule group water. The water has a long shelf life. After bottled water is stored for three years, its diameter, solvency, penetrability and activity do not change, and it is still sterile. The particle-energy multifunctional active water can be used in fields such as food, health care, pharmaceuticals, biology, environment protection, disease control, agriculture, military industry, engineering, energy source and daily life.

5 Claims, 4 Drawing Sheets

(51) Int. Cl.
*A23L 2/38* (2006.01)
*C02F 1/02* (2006.01)
*C02F 1/00* (2006.01)
*C02F 1/04* (2006.01)
*C02F 1/28* (2006.01)

(52) U.S. Cl.
CPC ............ *C02F 1/02* (2013.01); *A23V 2002/00* (2013.01); *C02F 1/001* (2013.01); *C02F 1/04* (2013.01); *C02F 1/281* (2013.01); *C02F 2305/08* (2013.01)

(56) References Cited

U.S. PATENT DOCUMENTS

| | | |
|---|---|---|
| 2009/0001012 A1 | 1/2009 | Kepner et al. |
| 2013/0228716 A1* | 9/2013 | Suetsuna ................ C22C 29/12 252/62.55 |
| 2015/0243433 A1* | 8/2015 | Sun ........................ B22F 9/04 148/102 |

FOREIGN PATENT DOCUMENTS

| | | |
|---|---|---|
| CN | 101684017 A | 3/2010 |
| CN | 101909714 A | 12/2010 |
| CN | 102249363 A | 11/2011 |
| CN | 102557162 A | 7/2012 |
| CN | 202898067 U | 4/2013 |
| CN | 103613177 A | 3/2014 |
| CN | 104370406 A | 2/2015 |
| CN | 104817124 A | 8/2015 |
| JP | 8-13009 A | 1/1996 |
| JP | 11-192492 A | 7/1999 |
| JP | 2003-339270 A | 12/2003 |
| JP | 2006-334505 A | 12/2006 |
| JP | 2006-334522 A | 12/2006 |
| JP | 2007-507407 A | 3/2007 |
| JP | 2013-212498 A | 10/2013 |

OTHER PUBLICATIONS

Lower S, "A Gentle Introduction to Water and its Structure", Internet citation, Mar. 3, 2003, pp. 1-7.
Lower S, "Water Cluster Pseudoscience", Internet citation, Dec. 9, 2002.

* cited by examiner

COMPOSITE MATERIAL, METHOD AND DEVICE FOR PREPARING PARTICLE-ENERGY MULTIFUNCTIONAL ACTIVE WATER

TECHNICAL FIELD

The present invention relates to composite material, method and device for preparing particle-energy multifunctional active water.

BACKGROUND OF THE PRESENT INVENTION

I. The Water in the Natural State

In real life, water is a basic substance, which people cannot be too familiar with, and every single day we can not get away from water. Without water, all organisms will be extinct. People know how to use water, and also know that water is a resource indispensable to human being's subsistence. The basic structure of a water molecule is $H_2O$, which is consisted of one oxygen atom and two hydrogen atoms. In nature, there are about 1300 types of water molecules. Most of the types of water molecules are rare in nature, and common types of water molecules do not exceed 20, of which approximately a half of the water molecules exist in nature for approximately 12 years, and the other half are eternal waters. Regarding how water was formed, a majority of the academic authorities believe that water is the product of the Big Bang. The Big Bang generated a huge amount of hydrogen and oxygen atoms, and afterward the hydrogen and oxygen atoms bound to generate water. A single water molecule exists as a triangle whose three atoms form a 104.52 degree angle. In the natural state, water is formed by the agglomeration of more than 10 water molecules, which is technically called "large molecule group water". Regarding why water exists as agglomerate, in theory it is considered that the reason is the degeneration and pollution of water. The chronic pollution of water causes the structure of water molecules to change, by changing from small molecule group water to large molecule group water with random arrangement, which reduces and degenerates the solvency, penetrability and diffusibility of water. Therefore, the water that exists in the natural state is large molecule group water. The various microelements that water contains are the result of the long-term mineralization of water.

The academic community has found by research that, the reason why water molecules are of an angular distribution rather than a linear distribution is that the side of oxygen has negative charges, the side of hydrogen has positive charges, and the positive charges are not evenly distributed around the negative charges, so their actions cannot be neutralized. The anode of a water molecule attracts the cathode of an adjacent water molecule, to cause the water molecules to adhere, to form the large molecule group water.

II. The Cause of the Formation of Large Molecule Group Water

It is already known that, at normal temperature, because of the unbalance of positive and negative charges, water molecules agglomerate to form large molecule groups. The formation of the large molecule groups is a physical process of the association of water molecules, and the opposite process is dissociation. Association is an exothermic process, while dissociation is an endothermic process. When the temperature of water increases, the degree of the association of the water decreases. Large molecule group water is dissociated as the temperature of water increases, and when water is heated to 100° C., the effect of the temperature enables the water molecules to have adequate energy to overcome the strong force of the hydrogen bonds to separate. When the temperature is higher than 100° C., water is in the gaseous state, and the water molecules are mainly constructed by single molecules. The covalent bonds between the hydrogen atoms and the oxygen atom of a water molecule are formed by sharing a pair of electrons. The degrees of sharing of the pair of electrons of water are unbalanced, and the oxygen needs the electrons more than the hydrogen. When the hydrogen and the oxygen are bound, mainly the strong force of the hydrogen bonds causes the water molecules to exist as agglomerates. Therefore, when heated to 100° C. water overcomes the force of the charges, and water molecules are separated. (in the process of heating the conductivity of water gradually falls, and when heated to 100° C. water is basically nonconducting.) Although large molecule group water can be dissociated into the single molecule state under the effect of temperature, when temperature decreases, the water molecules gradually associate and agglomerate again into large molecule group water. How to enable water molecules not to associate again at normal temperature is one of the important research topics of the academic community of primary substance.

III. The Possibility of Dissociation into Single Molecule Water

The academic community considers that the existence of the water in nature in the state of large molecule groups is because of the degeneration and pollution of the water. Separating water molecules from large molecule groups is consider as dissociating and restoring water into its original form. Therefore, many scholars in the primary substance field have been devoted to the research of this line for a long time. The developed countries successively developed magnetic water (1945, Belgium), electrolytic ion water (1999, Kyoto University, Japan) and reverse osmosis membrane purified water (1977, the DOW Chemical Company, USA). The magnetic water and the electrolytic ion water are prepared by employing magnetization and electrolysis to dissociate large molecule group water into small molecule group water. The reverse osmosis membrane purified water is prepared by applying magnetic force and pressure to an osmosis membrane to pass hydrogen and oxygen atoms, to similarly obtain small molecule group water. At the normal temperature, the small molecule group water gradually aggregates and associates again into large molecule group water. Generally, the duration for which it maintains the small molecule state is lower than 72 hours, and can reach 15 days in the sealing state, and under the effect of temperature it will immediately associate into large molecule group water. That can prove that its stability and activity have defects.

In nature, because the magnetic field intensities on the earth surface are different, the physical structures that waters present are different. A natural small molecule group water has been found in some areas of intense magnetic field on earth, and it is formed by the agglomeration of 5-7 water molecules. For example, such a natural small molecule group water has been found in the Bama region of Gangxi Province and Kunlun mountains of the Xinjiang Uygur Autonomous Region of China and the Caucasia area of Russia. Because people are gradually recognizing the extensive application prospect of the small molecule group water, just in the Bama region of Gangxi Province hundreds of people are gathering to exploit and utilize the small molecule group water. The natural small molecule group water will associate again in a short time after packaging, but the shelf life of the water can reach 12-18 months in the sealing state.

Technical Problem

The prior art cannot obtain small molecule water that is stable and has special activity.

Technical Solutions

The present invention creatively prepares a particle-energy multifunctional active water, which has special activity and energy effect, and can be used in various fields such as food, health care, pharmaceuticals, biology, environment protection, disease control, agriculture, military industry, engineering, energy source and daily life etc.

The present invention provides a composite material for preparing particle-energy multifunctional active water, wherein, the composite material contains the following components: Si, Re, Pt, Ge, Nb, Ni, Se and Mg.

Preferably, the components of the composite material and the parts by weight of the components are as follows:

Si 20-40,
Re 10-30,
Pt 10-30,
Ge 10-20,
Nb 5-15,
Ni 1-10,
Se 1-5,
Mg 1-5.

More preferably, the composite material consists of the following parts by weight of the components:

Si 33.13,
Re 21.87,
Pt 16.65,
Ge 12.75,
Nb 9.45,
Ni 2.25,
Se 2.17,
Mg 1.73.

Preferably, the composite material is of a sphere shape, a sphere shape with a through hole at the center, a sheet shape or an eggshell shape with an opening at one end.

The present invention further provides a method for preparing the composite material, wherein, the method comprises the following steps:

1) uniformly mixing silicon, rhenium, platinum, germanium, niobium, nickel, selenium and magnesium under vacuum;

2) magnetizing the mixture that is obtained in the step 1) in a magnetizer, wherein a magnetization intensity is 5-10 A/m, and a magnetization duration is 100-200 h;

3) placing the material that is magnetized in the step 2) in a forming mould, and conducting vacuum sintering; and 4) magnetizing the material that is obtained in the step 3) in a magnetizer, wherein a magnetization intensity is 80-100 A/m, and a magnetization duration is 100-300 h, to obtain the composite material.

As a preferable embodiment, the silicon, rhenium, platinum, germanium, niobium, nickel, selenium and magnesium in the step 1) are all nanometer-sized particles.

As a preferable embodiment, the magnetization intensity in the step 2) is 7 A/m, and the magnetization duration is 120-125 h.

Preferably, a sintering temperature in the step 3) is 800-1000° C.

More preferably, the vacuum sintering in the step 3) is sintering by conversion between a lower temperature and a higher temperature, wherein the material that is magnetized in the step 1) is placed in the forming mould, and, under vacuum, is firstly sintered at a temperature of 800-850° C. for 1-3 h, and then sintered at a temperature of 900-1000° C. for 10-15 h.

As a preferable embodiment, the magnetization intensity in the step 4) is 95-100 A/m, and a magnetization duration is 200-250 h.

The present invention further discloses a device for preparing particle-energy multifunctional active water by using the composite material, wherein, the device comprises:

a steam boiler, for heating water into high-pressure steam;

a high-pressure cylinder, connected to the steam boiler via a pipeline;

a particle-energy reactor, comprising a container and the composite material that is loaded in the container, wherein the container is provided with a steam inlet and a steam outlet, and the steam inlet is connected to the high-pressure cylinder via a pipeline;

a vacuum-type heat exchanger, comprising a container and the composite material that is loaded in the container, wherein the container is provided with a steam inlet that is connected to the steam outlet of the particle-energy reactor via a pipeline, the top of the container is provided with a steam outlet that is connected to the steam boiler via a pipeline, and the bottom of the container is provided with a water outlet; and an interactive-mode particle-energy water-purifying reactor, comprising a container and the composite material that is loaded in the container, wherein the container is provided with a water inlet and a water outlet, and the water inlet is connected to the water outlet of the vacuum-type heat exchanger via a pipeline.

As a preferable embodiment, the particle-energy reactor comprises:

a container, wherein the main container body is provided with a steam inlet, and the top of the container is provided with a steam outlet;

a supporting net, wherein the supporting net is a net-like structure of a shape the same as the cross-section of the container, and is provided within a lower part of the container, to separate the interior of the container into an upper loading zone and a lower aeration zone; and a blocking portion, consisting of a vertical blocking plate and a horizontal blocking plate that are integrally formed, wherein an upper side of the vertical blocking plate is integral with the horizontal blocking plate, two lateral sides of the vertical blocking plate cling to container walls, and a bottom side is laid on the supporting net; and one side of the horizontal blocking plate is integral with the vertical blocking plate, and other sides cling to the container walls; whereby, the blocking portion separates the upper loading zone in the container into a gas entering zone and a bypass zone, wherein, the steam inlet on the container corresponds to the location of the gas entering zone; and the composite material fills the loading zone.

Preferably, the container is provided with two steam inlets, of which an upper steam inlet is correspondingly located on the top of the gas entering zone, and a lower steam inlet is correspondingly located on the bottom of the gas entering zone.

As a preferable embodiment, the vacuum-type heat exchanger comprises:

a container, wherein the top of the container is provided with a steam outlet, and the bottom of the container is provided with a water outlet, wherein the main container body is provided with a steam inlet;

a first supporting net, wherein the first supporting net is a net-like structure of a shape the same as the cross-section of the container, and is provided within a lower part of the container, the composite material of a sphere shape is loaded on the first supporting net, to form a first heat exchange zone, and the steam inlet is correspondingly located below the first supporting net; and a second supporting net, wherein the second supporting net is a net-like structure of a shape the same as the cross-section of the container, and is provided within an upper part of the container, and the composite material of a sheet shape is loaded on the second supporting net, to form a second heat exchange zone;

wherein, an unfilled buffer zone is provided between the first heat exchange zone and the second heat exchange zone.

Preferably, the pipeline that connects the vacuum-type heat exchanger and the interactive-mode particle-energy water-purifying reactor is provided with a filtering device.

Preferably, the device comprises a plurality of the vacuum-type heat exchangers, wherein the steam inlets of the vacuum-type heat exchangers are individually connected to the steam outlet of the particle-energy reactor, and the steam outlets of the vacuum-type heat exchangers are individually connected to the steam inlet of the steam boiler.

Preferably, the device comprises a plurality of the interactive-mode particle-energy water-purifying reactors, which are in communication in series via a pipeline.

Preferably, the pipeline that is connected to the water outlet of the interactive-mode particle-energy water-purifying reactor is provided with a filtering device.

The present invention further provides a method for preparing particle-energy multifunctional active water by using the device, wherein, the method comprises:

1) introducing water into the steam boiler via a pipeline, heating to generate steam at 150-190° C., and feeding the steam via the high-pressure cylinder into the particle-energy reactor;

2) in the particle-energy reactor, the steam and the composite material contacting and interacting, wherein the steam temperature in the particle-energy reactor is maintained at 150-190° C.;

3) discharging the steam from the particle-energy reactor to the vacuum-type heat exchanger, and after the steam and the composite material in the vacuum-type heat exchanger contacting and conducting heat exchange, discharging the water via the water outlet, and circling the steam via the steam outlet back to the steam boiler; and 4) the water that is discharged from the vacuum-type heat exchanger entering the interactive-mode particle-energy water-purifying reactor, contacting with the composite material to conduct heat exchange till the temperature of the water is below 60° C., discharging, and filtering, to obtain particle-energy multifunctional active water.

As a preferable embodiment, the temperature of the steam in the step 1) and the step 2) is 145-155° C.

The present invention provides a particle-energy multifunctional active water, prepared by using the method.

Advantageous Effects

The present invention can achieve the following effects:
1. The present invention innovatively prepares particle-energy multifunctional active water. By detection, its structure is smaller than that of small molecule group water, and the specific gravity at normal temperature is 1.002-1.004 g/cm$^3$.

2. By detection, the particle-energy multifunctional active water that is prepared in the present invention is sterile water.

3. The stability and activity of the particle-energy multifunctional active water that is prepared in the present invention are far better than those of small molecule group water. In addition, the water has a long shelf life. After a bottle water is stored for three years, its diameter, solvency, penetrability and activity do not have any changes, and it is still sterile water.

4. The particle-energy multifunctional active water that is prepared by the present invention, due to its special activity and energy effect, can be used in various fields such as food, health care, pharmaceuticals, biology, environment protection, disease control, agriculture, military industry, engineering, energy source and daily life etc.

DETAILED DESCRIPTION OF THE PRESENT INVENTION

Figure 1:
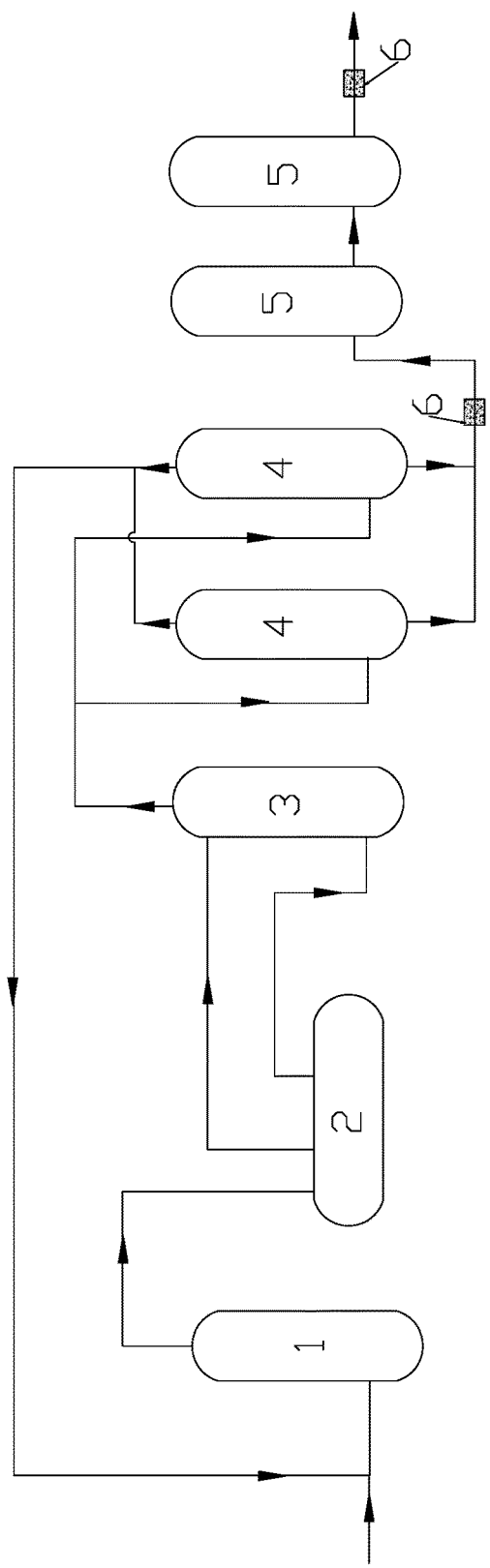
FIG. 1 is the schematic representation of the structure of the device for preparing particle-energy multifunctional active water of the present invention.

The present invention will be further illustrated below by referring to the drawings and the special examples, to enable a person skilled in the art to better understand and implement the present invention, but the examples are not taken as limiting the present invention.

The composite material for preparing particle-energy multifunctional active water of the present invention contains the following components: Si, Re, Pt, Ge, Nb, Ni, Se and Mg.

The composite material is prepared by using the following method:

1) uniformly mixing silicon, rhenium, platinum, germanium, niobium, nickel, selenium and magnesium under vacuum;

2) magnetizing the mixture that is obtained in the step 1) in a magnetizer, wherein a magnetization intensity is 5-10 A/m, and a magnetization duration is 100-200 h; 3) placing the material that is magnetized in the step 2) in a forming mould, and conducting vacuum sintering; and 4) magnetizing the material that is obtained in the step 3) in a magnetizer, wherein a magnetization intensity is 80-100 A/m, and a magnetization duration is 100-300 h, to obtain the composite material.

The composite material may be formed into (without limitation) the following shapes:

particle-energy sphere-shaped material, which has the diameter of 6-10 millimeters and is a solid sphere;

particle-energy egg-shaped sphere material, which has the maximum diameter of 43-82 millimeters and the wall thickness of 2-3 millimeters, is hollow, and has an opening at one end;

particle-energy round-sheet-shaped material, which has the diameter of 30-120 millimeters and the thickness of 2-5 millimeters; and particle-energy square-sheet-shaped material and particle-energy rectangular-sheet-shaped material, which has the planar size of 40×60 to 200×220 square millimeters and the thickness of 2-5 millimeters.

The method for preparing particle-energy multifunctional active water by using the composite material comprises the following steps:

1) introducing water into the steam boiler via a pipeline, heating to generate steam at 150-190° C., and feeding the steam via the high-pressure cylinder into the particle-energy reactor;

2) in the particle-energy reactor, the steam and the composite material contacting and interacting, wherein the steam temperature in the particle-energy reactor is maintained at 150-190° C.;

3) discharging the steam from the particle-energy reactor to the vacuum-type heat exchanger, and after the steam and the composite material in the vacuum-type heat exchanger contact and conduct heat exchange, discharging the water via the water outlet, and circling the steam via the steam outlet back to the steam boiler; and 4) the water that is discharged from the vacuum-type heat exchanger entering the interactive-mode particle-energy water-purifying reactor, contacting with the composite material to conduct heat exchange till the temperature of the water is below 60° C., discharging, and filtering, to obtain particle-energy multifunctional active water.

The present invention found, by quite a lot of experimentations, that the elementary particle energy that the composite material generates can make a vital effect on the water, so that large molecule water, after contacting with the composite material in specified conditions, generates small molecule water that is stable and has a special energy. The principle is speculated to be as follows: the energy particles (that is, the composite material of the present invention) has the effect of particle energy in the device, which enables the potential energy that is generated by the axial rotation movements of the various particles in the protons to change the structure of the water molecules, so that single water molecules can exist stably. Because the structure is changed, the water molecules lose the force of association, so cannot associate again into large molecule group water at the normal temperature. (the prepared particle-energy multifunctional active water will not associate again into large molecule group water even though repeatedly heated to 100° C. or refrigerated to −40° C.)

It is speculated theoretically that, the particle-energy multifunctional water may probably pair the protons and the neutrons in the nucleus of the water molecules to the stable state, so as to maintain the activity of the water molecules and enable them to have magnetism. In single water molecules of the particle-energy multifunctional water, on the basis of the basic structure of water molecules $H_2O$, the radius of the hydrogen atoms is 79 pm and the radius of the oxygen atoms is 70 pm. When two hydrogen atoms and an oxygen atom bind into a molecule, the bonding spacing between a hydrogen nuclei and the oxygen nuclei is 96 pm, and the outer electron spacing of a hydrogen atom and the oxygen atom at the room temperature is 240 pm. After the energy treating by the composite material, single water molecules can maintain the stable single molecule state at the room temperature for a long term. The viscosity of the prepared particle-energy multifunctional water is decreased, the solvency, the permeability and the dispersibility are all improved, and the activity is enhanced, without attenuation.

EXAMPLE 1

The composite material for preparing particle-energy multifunctional active water of this Example is prepared by mixing silicon nanoparticles, as the matrix, and other 7 nanometer-sized particles. The average length of this nanometer-sized material is 1-2 nanometers.

(I) The raw materials for preparing the composite material and the proportion thereof are as follows:

a. Silicon nanometer-sized particles, as the base of the composition of the composite material, whose mass accounts for 33.13% of the composition of the composite material;

b. Rhenium nanometer-sized particles, whose mass accounts for 21.87% of the composition of the composite material;

c. Platinum nanometer-sized particles, whose mass accounts for 16.65% of the composition of the composite material;

d. Germanium nanometer-sized particles with the purity of 97%, whose mass accounts for 12.75% of the composition of the composite material;

e. Niobium nanometer-sized particles, whose mass accounts for 9.45% of the composition of the composite material;

f. Nickel nanometer-sized particles, whose mass accounts for 2.25% of the composition of the composite material;

g. Selenium nanometer-sized particles, whose mass accounts for 2.17% of the composition of the composite material; and h. Magnesium nanometer-sized particles, whose mass accounts for 1.73% of the composition of the composite material.

(II) The method for preparing the composite material of this Example:

Mixing the above nanometer-sized particles of silicon, rhenium, platinum, germanium, niobium, nickel, selenium and magnesium under vacuum; after the material mixing, conducting particle-energy magnetization in a magnetizer, wherein in the magnetization process the magnetization intensity should reach 7 A/m, and the magnetization intensity is maintained for 123.25 h; after the magnetization performing sintering by conversion between a lower temperature and a higher temperature, by placing the material in a forming mould, and firstly sintering at 823.7° C. for 1.7 h, and then sintering at the constant temperature of 920° C. for 12 h; and after the sintering, conducting magnetization again, wherein the magnetization intensity is 97 A/m, and the magnetization is conducted at the normal temperature continuously for 235.5 h.

By using different molds, the composite material is formed into the following shapes:

particle-energy sphere-shaped material, which has the diameter of 6-10 millimeters and is a solid sphere or a hollow sphere;

particle-energy open-ended egg-shaped sphere material, which has the maximum diameter of 43-82 millimeters and the wall thickness of 2-3 millimeters, and is hollow;

particle-energy round-sheet-shaped material, which has the diameter of 30-120 millimeters and the thickness of 2-5 millimeters; and particle-energy square-sheet-shaped material and particle-energy rectangular-sheet-shaped material, which has the planar size of 40×60 to 200×220 square millimeters and the thickness of 2-5 millimeters.

Figure 2:
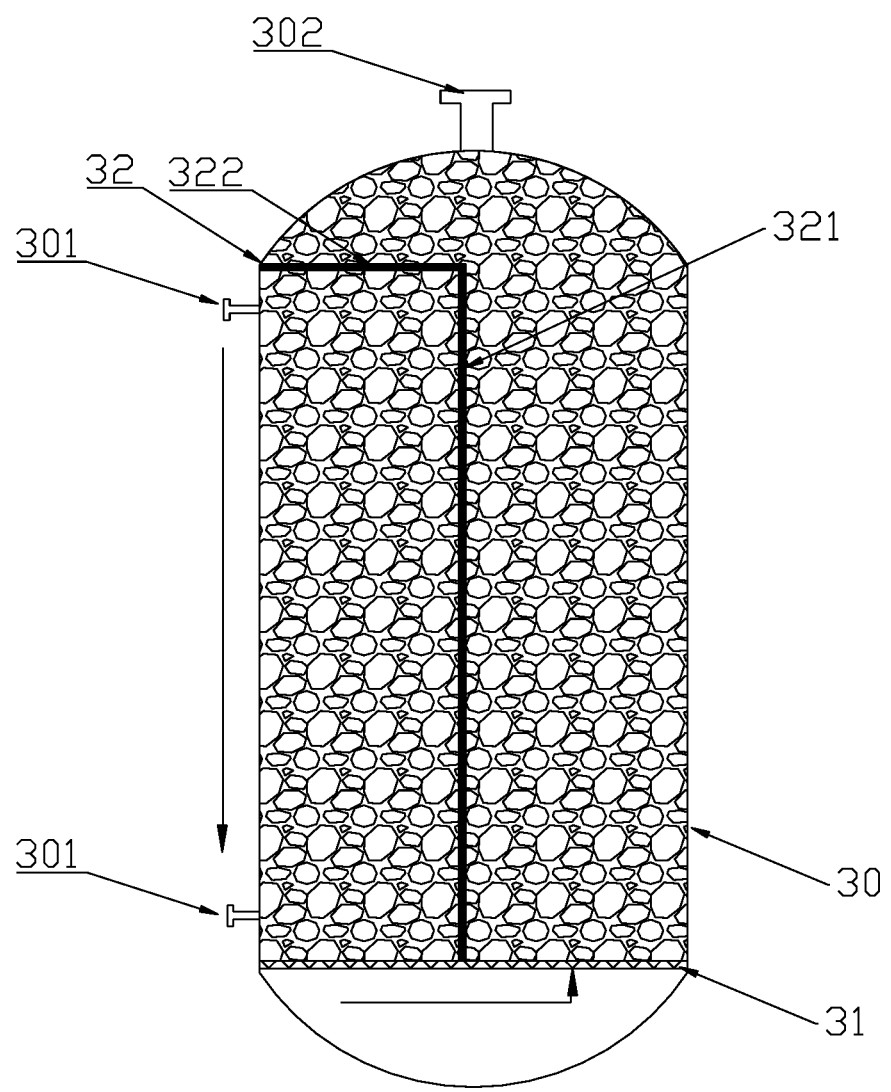
FIG. 2 is the schematic representation of the structure of the particle-energy reactor of the device for preparing particle-energy multifunctional active water of the present invention.
Figure 3:
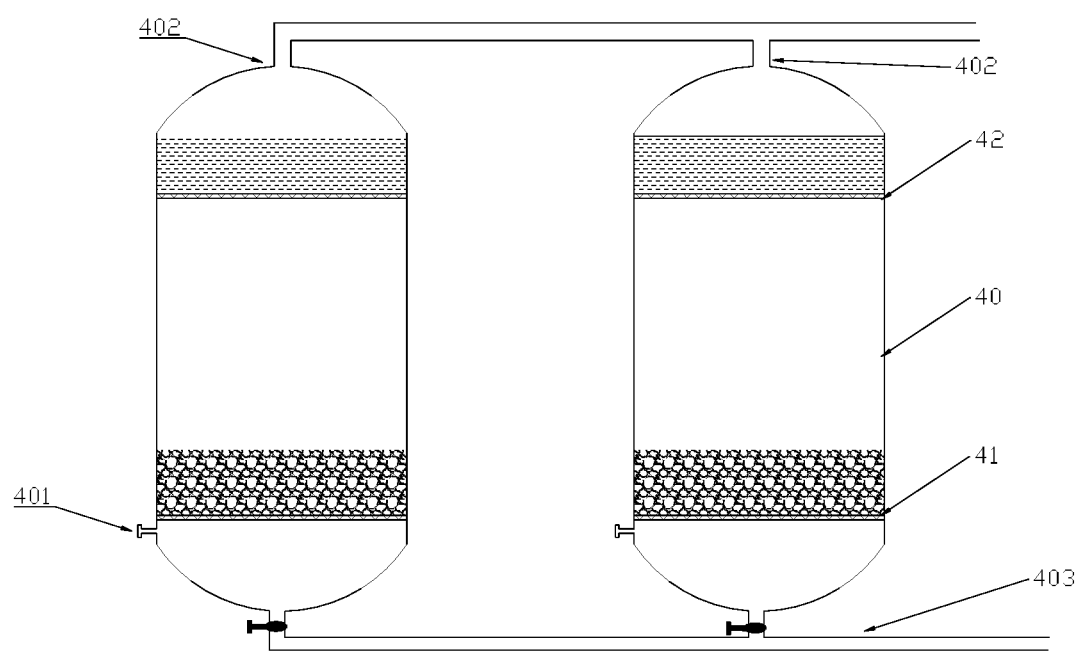
FIG. 3 is the schematic representation of the structure of the vacuum-type heat exchanger of the device for preparing particle-energy multifunctional active water of the present invention.

(III) The method for preparing particle-energy multifunctional active water by using the composite material in a specific device of this Example is specially as follows:

Referring to FIGS. 1-3, the device for preparing particle-energy multifunctional active water of the present invention comprises:

a steam boiler 1, for heating water into high-pressure steam;

a high-pressure cylinder 2, connected to the steam boiler 1 via a pipeline;

a particle-energy reactor 3 (as shown in FIG. 2), comprising:

a container 30, wherein the main container body is provided with a steam inlet 301, the top of the container is provided with a steam outlet 302, and the steam inlet 302 is connected to the high-pressure cylinder via a pipeline;

a supporting net 31, wherein the supporting net 31 is a net-like structure of a shape the same as the cross-section of the container 30, and is laid within the lower part of the container 30, to separate the interior of the container 30 into an upper loading zone and a lower aeration zone; and a blocking portion 32, consisting of a vertical blocking plate 321 and a horizontal blocking plate 322 that are integrally formed, wherein the upper side of the vertical blocking plate 321 is integral with the horizontal blocking plate 322, the two lateral sides of the vertical blocking plate 321 cling to the container walls, and the bottom side of the vertical blocking plate 321 is laid on the supporting net 31; one side of the horizontal blocking plate 322 is integral with the vertical blocking plate 321, and other sides cling to the container walls; whereby, the blocking portion 32 separates the upper loading zone in the container into a gas entering zone and a bypass zone, wherein, the steam inlet 301 on the container corresponds to the location of the gas entering zone, in a preferable embodiment of the present invention, the container is provided with two steam inlets 301, of which an upper steam inlet is correspondingly located on the top of the gas entering zone, and a lower steam inlet is correspondingly located on the bottom of the gas entering zone;

a sphere shaped or open-ended eggshell shaped composite material, which is packaged in a steel wire net bag and fills the loading zone; and a vacuum-type heat exchanger 4 (as shown in FIG. 3), comprising:

a container 40, wherein the top of the container is provided with a steam outlet 402 that is connected to the steam boiler 1 via a pipeline, and the bottom of the container is provided with a water outlet 403, wherein the main container body is provided with a steam inlet 401 that is connected to the steam outlet 302 of the particle-energy reactor via a pipeline;

a first supporting net 41, wherein the first supporting net 41 is a net-like structure of a shape the same as the cross-section of the container, and is laid within the lower part of the container, the composite material of a sphere shape or an open-ended eggshell shape is loaded on the first supporting net 41 (the composite material is packaged in a steel wire net bag and then is load on the first supporting net 41), to form a first heat exchange zone, and the steam inlet is correspondingly located below the first supporting net; and a second supporting net 42, wherein the second supporting net 42 is a net-like structure of a shape the same as the cross-section of the container, and is laid within the upper part of the container, the composite material of a sheet shape is loaded on the second supporting net 42, to form a second heat exchange zone;

wherein, an unfilled buffer zone is provided between the first heat exchange zone and the second heat exchange zone.

In a preferable embodiment of the present invention, the device comprises a plurality of the vacuum-type heat exchangers 4, wherein the steam inlets 401 of the vacuum-type heat exchangers are individually connected to the steam outlet 302 of the particle-energy reactor, and the steam outlets 402 of the vacuum-type heat exchangers are individually connected to the steam inlet of the steam boiler.

Figure 4:
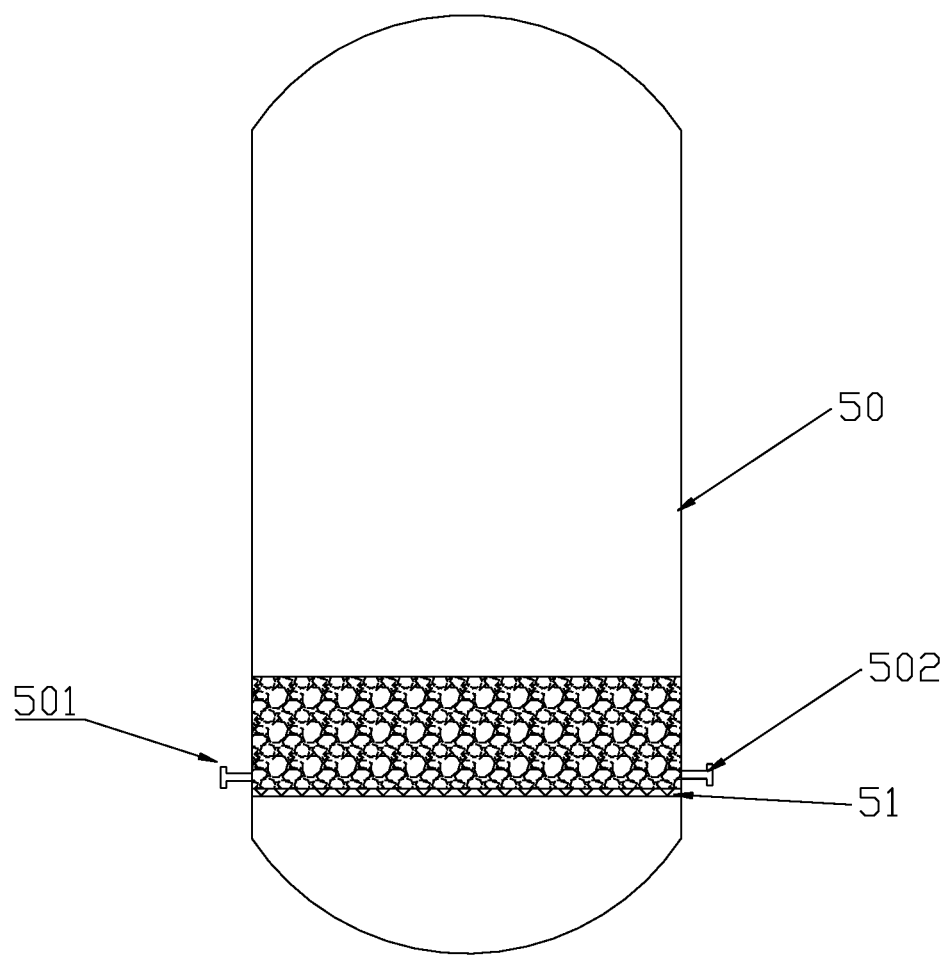
FIG. 4 is the schematic representation of the structure of the interactive-mode particle-energy water-purifying reactor of the device for preparing particle-energy multifunctional active water of the present invention.

As shown in FIG. 4, the interactive-mode particle-energy water-purifying reactor 5 comprises a container 50, a supporting net 51 and the composite material that is loaded on the supporting net (which can be unfilled), wherein the main container body is provided with a water inlet 501 and is provided with a water outlet 502, and the water inlet 501 is connected to the water outlet 403 of the vacuum-type heat exchanger 4 via a pipeline. As shown in FIG. 1, the device comprises a plurality of the interactive-mode particle-energy water-purifying reactors 5, which are conected in series via a pipeline.

In the device of the present invention, the pipeline that connects the vacuum-type heat exchanger 4 and the interactive-mode particle-energy water-purifying reactor 5 is provided with a filtering device 6.

The method for preparing particle-energy multifunctional active water by using the above device of this Example comprises:

1) introducing water into the steam boiler 1 via a pipeline, heating to generate steam at 145-155° C., and feeding the steam via the high-pressure cylinder 2 into the particle-energy reactor 3. The choosing and utilization of the water: high-quality river water, lake water and reservoir water can all be used; groundwater should be from a non-limestone strata; tap water can be used after scavengers are removed; and introduced extraneous waters should be filtered before storage.

2) in the particle-energy reactor 3, conducting the contact reaction between the steam and the composite material, wherein the steam temperature in the particle-energy reactor 3 is maintained at 145-155° C. The fed high-temperature steam should be subject to the cycling thermal potential energy reaction in the particle-energy reactor 3. In the high temperature condition, the particle-energy core material conducts high-efficiency magnetization on the steam, which refers to utilizing the particle-energy potential energy effect at high temperature and high pressure to change the structure of the water molecules in the steam state. The particle-energy reactor has the effect of vacuum magnetization, which enables the particle energy to stably act on the preparation process of the particle-energy multifunctional water. After the high-temperature steam enters the particle-energy reactor, the particle-energy potential energy of the particle-energy composite material intensifies as the temperature increases, and acts on the steam. After the high-temperature steam is subject to the high-intensity and stable particle potential energy magnetization process of the particle-energy composite material, the structure of the water molecules is changed. By maintaining the magnetic field of that intensity, the flux density that the molecular separation process requires can be reached. The water molecules that have been magnetized by the particle potential energy magnetization enter the vacuum-type heat exchanger in the gaseous state.

3) feeding the steam that has been magnetized in the particle-energy reactor 3 into the vacuum-type heat exchanger 4, and conducting the heat exchange between the two layers of particle-energy field; separating the steam and the formed water by the vacuum-type heat exchanger 4; feeding the magnetized single molecule water that has been formed downward into the interactive-mode particle-energy water-purifying reactor 5; and returning the vaporous water molecules (steam) that are still in the steam state and is not completely stable to the steam boiler 1 via a pipeline to be heated again. The vacuum-type heat exchanger 4 conducts the heat interaction between the water and the steam by vacuum exchange, and realizes the even distribution of water molecules under the effect of particle-energy potential energy. In the interaction process of the particle-energy magnetic field intensity and the cyclic magnetization, the water stably exists in the single molecule state, and enters the interactive-mode particle-energy water-purifying reactor via a downstream pipeline. The unstable water molecules (gaseous state) return to the steam boiler 1 via an upstream pipeline to be heated again.

4) transporting the particle-energy multifunctional active water produced in the vacuum-type heat exchanger 4 to the interactive-mode particle-energy water-purifying reactor 5, wherein this process is mainly to transfer the temperature of the water from the high temperature water to the normal temperature water; the heat of the water gradually releasing in the water container, and when the water is below 60° C., conducting primary filtering on the water; and transporting the primarily filtered water to a water storage pot, conducting fine filtration after the water is cooled to the normal temperature, and feeding the fine filtered water to a water pot for the finished product water for storage. After the interactive-mode particle-energy water-purifying reactor 5 sends the formed particle-energy multifunctional water from the vacuum-type heat exchanger to the apparatus, the water gradually turns from high temperature to normal temperature. In the process, the structure of the water is stabilized under a certain low magnetic field intensity, and is interchanged to be subject to purifying reaction.

(IV) The detection and verification of the properties of the particle-energy multifunctional active water that is prepared in this Example:

A. Regarding the Structure of the Water Molecules:

Under transmission electron microscopy, the structure of the particle-energy multifunctional active water presents the appearance of randomly arranged small molecule groups, whose diameters are below 1 nm, which is smaller than those of conventional small molecule group water (large molecule group water refers to the water molecule group that is formed by the aggregation of more than 10 water molecules, and its diameter is greater than 2.6 nm; and small molecule group water refers to the water molecule group that is formed by the aggregation of 5-7 water molecules, and its diameter is 1.1-1.6 nm). Under scanning tunneling microscope, the molecules of the particle-energy multifunctional active water are arranged by single water molecules. Note: the resolution of the transmission electron microscopy (ST) is one millionth of a millimeter, and the resolution of the scanning tunneling microscope (STM) is 1 part per hundred million of a millimeter.

B. Regarding the Examination on the Water Quality of the Particle-Energy Multifunctional Active Water:

The results of the detection by National Institute of Environmental Health, Chinese Center for Disease Control and Prevention can be seen in the following table:

Physical and Chemical Indicators

| Serial No. | Detection Item | Unit | Requirement by National Standards | Detection Result | Item Conclusion |
|---|---|---|---|---|---|
| 1 | Chromaticity | Degree | ≤15 | <5 | Qualified |
| 2 | Turbidity | NTU | ≤1 | 0.33 | Qualified |
| 3 | Odor and Smell | Description | Should Not Exist | None | Qualified |
| 4 | Material Visible by Bare Eye | Description | Should Not Exist | None | Qualified |
| 5 | pH | / | 6.5-8.5 | 8.08 | Qualified |
| 6 | Total Hardness | mg/L | ≤450 | 9.0 | Qualified |
| 7 | Aluminum | mg/L | ≤0.2 | 0.054 | Qualified |
| 8 | Iron | mg/L | ≤0.3 | <0.01 | Qualified |
| 9 | Manganese | mg/L | ≤0.1 | <0.005 | Qualified |
| 10 | Copper | mg/L | ≤1 | <0.01 | Qualified |
| 11 | Zinc | mg/L | ≤1 | 0.016 | Qualified |
| 12 | Sulfate | mg/L | ≤250 | 1.15 | Qualified |
| 13 | Chloride | mg/L | ≤250 | 0.75 | Qualified |
| 14 | Total Dissolved Solids | mg/L | ≤1000 | 20 | Qualified |
| 15 | Oxygen Consumption | mg/L | ≤3 | 0.77 | Qualified |
| 16 | Volatile Phenols | mg/L | ≤0.002 | <0.002 | Qualified |
| 17 | Anionic Synthetic Detergent | mg/L | ≤0.3 | <0.10 | Qualified |
| 18 | Cyanide | mg/L | ≤0.05 | <0.002 | Qualified |
| 19 | Fluoride | mg/L | ≤1.0 | 0.06 | Qualified |
| 20 | Arsenic | mg/L | ≤0.01 | <0.0005 | Qualified |
| 21 | Selenium | mg/L | ≤0.01 | <0.0005 | Qualified |
| 22 | Mercury | mg/L | ≤0.001 | <0.00005 | Qualified |
| 23 | Cadmium | mg/L | ≤0.005 | <0.0001 | Qualified |
| 24 | Chromium (+6) | mg/L | ≤0.05 | <0.004 | Qualified |
| 25 | Nitrate Nitrogen | mg/L | ≤10 | 0.28 | Qualified |

-continued

| Serial No. | Detection Item | Unit | Requirement by National Standards | Detection Result | Item Conclusion |
|---|---|---|---|---|---|
| 26 | Lead | mg/L | ≤0.01 | <0.0005 | Qualified |
| 27 | Trichloromethane | mg/L | ≤60 | <0.5 | Qualified |
| 28 | Carbon Tetrachloride | mg/L | ≤2 | <0.1 | Qualified |

It can be seen in the above table that, the contents of the minerals and ions and hazardous substances in the particle-energy multifunctional active water are far below the national standards.

Microorganism Indicators

| Detection Item | Detection Result | Stand Limit Value |
|---|---|---|
| Total Bacterial Count (CFU/mL) | 0 | 100 |
| Total *Escherichia Coli* (MPN/100 mL) | Undetected | Not Detectable |
| *Escherichia Coli* (MPN/100 mL) | Undetected | Not Detectable |

It can be seen in the above table that, the particle-energy multifunctional active water that is prepared in this Example is completely sterile water. That is what the conventional small molecule waters so far cannot achieve.

C. Regarding the Density of the Particle-Energy Multifunctional Active Water

The detection method: accurately measuring 1 m$^3$ of the particle-energy multifunctional active water, and weighing.

By the detection, it is found that at the normal temperature, the density is 1.002-1.004 g/cm$^3$, and the water is so far the only water whose density exceeds 1 g/cm$^3$ (the density of the ordinary water at the normal temperature is 0.998 g/cm$^3$).

D. Regarding the Radioactivity

The particle-energy multifunctional active water of the present invention was detected by Analytical laboratory of Beijing Research Institute of Uranium Geology.

The first test approach: DZ/T 0064, 80-1993<Groundwater test method, assaying 39 elements including lithium by plasma mass spectrometry>, instrument model: ELEMENT XR Plasma mass spectrometer The detection results are as shown in the following table (unit: µg/L):

| Li | Be | Sc | Ti | V | Mn | Cr | Co | Ni | Cu |
|---|---|---|---|---|---|---|---|---|---|
| 2.08 | 0.005 | 13.0 | 1.65 | 0.830 | 1.20 | 0.226 | 0.060 | 1.14 | 0.374 |
| Zn | Ga | Rb | Y | Nb | Mo | Cd | Sb | Cs | La |
| 19.1 | 0.377 | 27.3 | 0.094 | 0.047 | 0.096 | 0.017 | 0.070 | 0.823 | 0.127 |
| Ce | Pr | Nd | Sm | Eu | Gd | Tb | Dy | Ho | Er |
| 0.218 | 0.034 | 0.099 | 0.020 | 0.003 | 0.019 | 0.003 | 0.017 | 0.002 | 0.009 |
| Tm | Yb | Lu | W | Tl | Pb | Bi | Th | U | Sr |
| 0.003 | 0.012 | 0.003 | 0.477 | 0.055 | 0.760 | 0.015 | 0.055 | 0.078 | 4.07 |
| | In | | | Zr | | | Hf | | |
| | 0.004 | | | 0.674 | | | 0.016 | | |

The second test approach: DZ/T 0184-19-1997 "Zinc reduction assay for hydrogen isotopes in water", and DZ/T 0184-21-1997 "Oxygen isotopes and carbon dioxide in natural water—assay by water-balance method". Instrument model: MAT 253. The detection results are as follows:

| $\delta D_{V\text{-}SMOW}$ (‰) | $\delta^{18}O_{V\text{-}SMOW}$ (‰) |
|---|---|
| −30.7 | −6.2 |

It can be seen in the first and the second test approaches that, the particle-energy multifunctional active water of the present invention does not contain radioactive elements, and thus does not have radioactivity.

E. Stability

Even heating the particle-energy multifunctional active water that is prepared in this Example to 100° C. cannot change the functional characteristics and activity of the particle-energy multifunctional active water, and cannot cause the particle-energy multifunctional active water to be associated and reduced into the normal water. After standing for 3 years, by verifying by activity experimentation, its activity does not have any deterioration.

F. Activity

The properties of the particle-energy multifunctional active water of the present invention are not changed after long-term storage, which is speculated to probably be related to the activity nature of the particle-energy multifunctional active water. Because the particle-energy multifunctional active water has no radioactive source, it does not have radioactivity. The reasons why the particle-energy multifunctional active water can be stored for a long term without activity attenuation has not been understood. It is guessed from the production process and other aspects that the activity source of the particle-energy multifunctional active water may be magnetism. Several small scaled experiments are as follows:

a. The particle-energy multifunctional active water that is prepared in this Example are placed into a glass, plastic or aluminum container and sealed (500 g container), and beer, white spirit or cigarette closely adheres to the wall of the container. The energy that the water releases can penetrate the container. After two hours, the tastes of the wines and the cigarette obviously change, and their mouthfeels are obviously improved.

b. The particle-energy multifunctional active water is placed into a water bed that is made from a polymer material, and after a person lies on it for 30-45 minutes, his fatigue completely disappears. A patient of cervical spondylosis simply places a plastic bottle of the particle-energy multifunctional active water under the neck before sleeping, and after 2 hours the pain sense significantly alleviates or even disappears.

G. Nuclear Magnetic Resonance

The nuclear magnetic resonance is performed at 48-50 Hz.

(V) The applications of the particle-energy multifunctional active water that is prepared in this Example 1. The Particle-Energy Multifunctional Active Water and Modern Biology Regarding the water molecule groups that exist in the natural state, large molecule group water refers to the water molecule group that is formed by the aggregation of more than 10 water molecules, and its diameter is greater than 2.6 nm; and small molecule group water refers to the water molecule group that is formed by the aggregation of 5-7 water molecules, and its diameter is 1.1-1.6 nm.

In modern biology, the transmembrane protein channels of human cell walls are assayed, and the transmembrane protein water channels of human cell walls are 2 nm. In a single water molecule of the particle-energy multifunctional water, the spacing between the outer electrons of the hydrogen atom and the oxygen atom is 240 pm at room temperature, and 390 pm in the vapor state. Therefore, the particle-energy multifunctional water can directly pass through the cell water channels and enter each of the cells and the red blood cells; can satisfy the requirements of each of the nucleuses of human body on the numbers of water molecules and growth factors for conducting metabolism; and can improve the cellular metabolism function of human body which has been deteriorated due to oversized water molecules.

In 1991 scientists of Germany found that the cell membranes of human being have water channels that have diameters of 2 nm and can allow water and ionized nutrient substances to together pass through the cells, which are called cell water channels. Small molecule group water, by the effect of the electrostatic force of the proteins of human body, can easily pass through the water channels of cell membranes, while the water molecule groups that are formed by more than 10 water molecules are difficult to enter the interior of cells.

In 2000, scientists of the United States of America shot the first photograph of the water channel proteins of cell membrane worldwide by using photomicrography, which again proves that the cell water channels are 2 nm, and thus water molecules that are larger than 2 nm are difficult to enter the interior of cells. In addition, human cells can accommodate at most 10 water molecules.

In the upgrowth period, the electrostatic forcing of the proteins of human body itself is very strong, and can separate large molecule group water to enable it to enter cells. After the upgrowth period, with the increasing of age, the ability to forcing of human body itself gradually weakens, and its capacity of separating also increasingly lowers.

Science proves that, the cell water channels of human body are hexagonal channels that are wrapped by six protein subunits, and by the action of the electrostatic force of the proteins, water molecules one by one pass through the channels to enter the cell, conduct hydration, and assimilate and excrete nutrient substances and metabolites.

The academic community has verified that, water is a medium that is indispensable to the nutrition absorption of human cells and physiological activities, and the water channels of cell walls are through and thus cell walls are not sealed shells. The academic community proposes that the cause of the cataplasia and depletion of human cells is that "the water exchange of cells is hindered".

In principle, the particle-energy multifunctional active water that is prepared in the present invention is a single molecule water, and it can very easily enter the interior of cells, thereby restoring the original functions of human cells, and promoting cell growth and antibacterial and antivirus actions.

2. The Pharmaceutical uses of the Particle-Energy Multifunctional Active Water

The trace mineral elements and the trace metal elements that the particle-energy multifunctional active water contains are all in the ion states, the contents of hazardous substances are extremely low and the water is sterile. Therefore, the water reaches the grade of pure water, and can be applied to medical treatment. By being administrated on patients by vein instillation, it can decompose the blood fat, blood sugar and other deposits in blood and discharge them out of the body, and cells and genes are repaired to a certain extent.

A. Cancers

Voluntary clinical trial for cancers was conducted in a hospital in Hebei Province. The subject is a 30-year old female patient of late-stage breast cancer. The manner of the trial is by formulating a vein drop liquid from a cancer therapeutic drug and the particle-energy multifunctional active water, treating the patient by vein instillation, and in the treating process conducting gene detecting on the patient at all times. The result is as follows: at first, the expressions of the immunocompetence genes CD4 and PRF1, the oxidation resistance gene SOD-2 and the toxin metabolic enzyme gene CYP1 A2 are abnormal, and as the treating proceeds, the expressions of some of the genes restore to the normal states, and the SOD-2 gene is in the process of restoring. It can be seen from the results of gene detecting that, the patient's condition has obviously improved.

Voluntary clinical trial for cancers was conducted in a hospital in the City of Guangzhou. The subject is a 40-year old cancer patient. The manner of the trial is by dissolving an injection cancer medicine in the particle-energy multifunctional active water of the present invention and conducting vein instillation. After the treatment for 6 months, cancer cells cannot be detected.

B. Hypertension

The subject is a hypertension patient over 50-year old. The manner of the trial is by vein instillation, and the trial quantity is 250 mL per day. After continually conducting the instillation for 6 days, the quantity is increased to 500 mL per day. After 9-10 days, the blood pressure restores to the normal level.

C. Hypotension

The subject is a hypotension patient. The trial quantity is 500 mL per day, and the manner of the trial is by vein instillation. During the instillation there were no adverse reactions, and after continually conducting the instillation for several days, the blood pressure restores to the normal level.

D. Allergy

The subject is an allergy patient. The manner of the trial is by vein instillation. After the first day of the instillation, the allergy symptom aggravated. From the second day the allergy symptom improved and alleviated. After continually conducting the instillation for 9 days, the allergy symptom disappeared.

E. Cardiovascular and Cerebrovascular Diseases and Cardiac Extra Systole

The particle-energy multifunctional active water has significant effect on softening heart and cerebral vessels and mitigating cardiovascular and cerebrovascular diseases. After being subject to artery instillation by 500 mL per day, a patient of cardiovascular and cerebrovascular diseases's blood viscosity was greatly reduced, the obstruction state was obviously improved, and the blood fat and deposits in the blood were decomposed and discharged out of the body via the urethra. Regarding cardiac extra systole, the subject is a male patient of cardiac extra systole, and was subject to vein instillation by 500 mL per day. After the instillation by two bottles, the extra systole symptom was mitigated, after the instillation by 11 bottles, the extra systole symptom has not emerged till now. In addition, the patient had severe insomnia, and after the instillation by 4 bottles, he no longer had insomnia, and his tuberculosis block, which was calcified years ago, had a reduced shadow on the lung after the instillation treatment.

F. Others

After being subject to the vein instillation for 30 minutes, a few subjects had phenomena of intestinal tract movement and farting. After being subject to the vein instillation for one hour, some of the subjects had urge to urinate, and the time when most of the subjects had urge to urinate was after 2 hours. During or after the instillation, at the first urination, the urines of most of the subjects were of the color of Cola, and had superfine particles in them (by detecting, they were mainly waste cell tissues that were generated by metabolism). The urines of the small part of the subjects were pink, and regarding those having pink urine, after the second urination or several times of the instillation, their urines sometimes were of the color of Cola.

So far, the urine of one subject is of the color of light blue (he works in a lead zinc mine, and that may be because of exceeding contents of lead and zinc), and the urine of one subject is of the color of light green (he works in a copper mine, and that may be because of exceeding content of copper).

The urines that patients of diabetes excreted after being subject to the instillation were of the colors of yellow or Cola, and they all had foam. The urines of drug addict patients after being subject to the instillation were of the color of soy sauce.

The principle of the above effects of the particle-energy multifunctional active water of the present invention is speculated to be that: the particle-energy multifunctional active water itself has totally no therapeutic action on the diseases, and the significant effects that appeared after the instillation are because of the water can act on human cells and the genes in nucleuses, and can transport proteins and substances that the cells need into the cells, and provide the material basis for the reparation, surviving and regeneration of the cells and cell tissues. Therefore, the water activates the original functions of human body itself, and restores the functions of human body itself. The particle-energy multifunctional water does not only have reparation effects on the cell tissues and genes with atrophy and pathology of human body, but can also metabolize the impurity and deposits in blood. It should be in particular worth noting that, the particle-energy multifunctional water does not only have excellent effects on the reparation and growth of human cells, but also have superior antibacterial and antivirus effects, and can decompose and clear the germs, aged cells and deposits in the body and the blood.

3. The Use of the Particle-Energy Multifunctional Active Water in Daily Healthcare The particle-energy multifunctional active water can also be used for oral drinking and daily healthcare. It can gradually restore the original functions of human cells, and promote cell growth and antibacterial and antivirus actions. The quality of the particle-energy multifunctional active water will not deteriorate, so its function will not be degraded because of long-time storage.

1). By being drunk three times per day in the morning, noon and evening by 50 mL each time, the water can improve the movement of intestinal tract, smooth gas discharging, condition liver and spleen and promote the assimilation in the intestine and stomach and metabolism. A patient of chronic constipation obtained obvious effect after drinking for 5-7 days, wherein the defecation became smoother, and the fart was odorless. The water has obvious amelioration on insomnia, gastroenteritis, gastric acid, gastralgia, gastric ulcer, defatigation syndrome (overfatigue) and so on. For most of intestinal tract diseases, the disorders disappeared after the drinking of the particle-energy multifunctional active water for 15 days. Hot drinking will obtain better effects, and at night, drinking before sleeping is better.

2). For patients of hypertension, by the daily drinking quantity of 1500-2000 mL, the effect was significant after three days. After continually drinking for 5-7 days, the frequency can be reduced to three times per day and 100 mL each time. The degree of vasoconstriction can be effectively mitigated.

3). Patients of eye function defects can directly drip the particle-energy multifunctional active water into eyes, by randomly several times per day and a plus one time before sleeping. The particle-energy multifunctional active water can gradually repair the eye cells and restore the original functions of the eyes. No additional medicines are required to be added. The usage manner is by injecting the water into an empty eye medicine bottle by using a 10 or 20 mL syringe and conducting instillation.

4). Patients of dirty teeth and linguae neonatal jaundice may, in addition to drinking according to the above term 1), one time each in morning and evening per day, hold the particle-energy multifunctional active water in the mouth by half of the mouth for 5 seconds, and brush the teeth by using a common toothpaste for 20-30 seconds (longer will be better). That can immediately clean the tartar and the yellow fur. For patients of allergic rhinitis or rhinobyon, by dripping two drops of the water into each of the nostrils and breathing once, the nose can ventilate at once, and moreover rhinitis can be immediately mitigated.

5). As for the diseases like dermatitis, acne, freckle, mottling and tineas etc., wiping those by using the particle-energy multifunctional active water obtained obvious effects. The effects were better if a medicine was added into the particle-energy multifunctional active water. As for patients of dermatophytosis, washing the affected part by using a few drops of the particle-energy multifunctional active water can immediately stop the itch, and after washing for 1 or 2 days the dermatophytosis cured. As for bromhidrosis, spraying or wiping the particle-energy multifunctional active water at the armpits can immediately stop the odor.

6). As for the beauty treatment function, the the particle-energy multifunctional active water was mixed with the proportion of 30-50% with commercially available products for skin protecting and skin whiting, and the mixture can be used after 1 hour when they were naturally dissolved. The multifunctional water was used to spread on skin at all times, and obtained wet skin sense. By spreading a small amount of the water at the hairy roots and pressing for 30 seconds, hair can be soft and bright, and the long-term usage has effect of promoting hair growth. A facial mask was used before sleeping, and after the facial mask got dried, the facial mask was wetted to be soft again by using the water with small water spraying.

7). As for cervical spondylosis or cervical disease, the particle-energy multifunctional active water may be heated to an proper temperature and placed into a hot-water bag, and be placed at the cervical vertebrae before sleeping. For the use hereafter, the hot-water bag was placed in a basin and heated by hot water for repeated use. Dysmenorrhea of women can also be treated by the method, by placing the hot-water bag at the lower abdomen. The particle-energy multifunctional active water should not be used together with other kinds of water, and the water that has been placed in a hot-water bag cannot be drunk, but can be repeatedly used for a long term.

8). The particle-energy multifunctional active water also has the function of alleviating a hangover, by drinking 150-200 mL of the particle-energy multifunctional active water after getting drunk. The drinker can feel the effect immediately upon drinking the water, and can get sober after approximately 15-20 minutes. After drinking the particle-energy multifunctional active water, even if the drinker drinks the wine, there is no alcoholic breath, and he will not feel uncomfortable completely.

The particle-energy multifunctional active water has superior effect on wines. Any type of white spirits, by merely before drinking adding 3-5 g per bottle of the particle-energy multifunctional active water, shaking, and waiting for 5 minutes, can have very soft taste, sweet fragrance and no spicy irritation. If a forged wine is added with the particle-energy multifunctional active water, it will get a bitter mouthfeel, but an originally brewed wine will have the above-mentioned effect. If a bottle of white spirit is placed between two bottles of the particle-energy multifunctional active water, after 12 hours the white spirit can also become soft, sweet and fragrant. The water has the same effect on beers and grape wines.

9). As for common cold, dissolving a bag of particle medicine of cold with the hot particle-energy multifunctional active water three times per day will obtain good effect.

10). As for menstruation discomfort of women, there are two approaches of using the water, wherein one is by heating the particle-energy multifunctional active water and drinking, and the other is by placing the particle-energy multifunctional active water into a hot-water bag, placing hot water into a basin before using to warm the hot-water bag, and placing hot-water bag on the lower abdomen. By that, dysmenorrhea can be significantly mitigated.

11). As for mosquito biting, insect biting, bee sting and skin tickling, after the sites were coated by the particle-energy multifunctional active water, the itch can be immediately stopped, and the inflammation dots can gradually disappear. The effect of sunscreen was excellent too, by merely spreading the water on the exposed parts.

12). The particle-energy multifunctional active water has better effects on fire injury, red injury and burning scald than conventional medicines (as stated by the user). The patients only need to spray a small amount of the particle-energy multifunctional active water to the affected parts multiple times per day, and the effect is extraordinarily significant. That is because the particle-energy multifunctional active water has superior effect on promoting cell growth. As for scratching and wound, washing the wound by using the particle-energy multifunctional active water can immediately stop the hurt, and after the washing the wound may be simply tied up. That is because the particle-energy multifunctional active water has antibacterial effect. The particle-energy multifunctional active water is sterile, which can be seen in the detection report of the Chinese Center for Disease Control and Prevention.

13). The particle-energy water has interaction of physical and chemical characteristics with photons (light quantums), and they can convert energy to each other. Therefore, the particle-energy multifunctional active water has excellent sunscreen effect. However, its storage should be protected form light. The particle-energy multifunctional active water has another two special characteristics, wherein one is that its quality will not deteriorate regardless of the storage duration, and the other is that its function will not be weaken due to long-term storage.

4. The Use of the Particle-Energy Multifunctional Active Water in Rehabilitation Treatment The rehabilitation treatment by using the particle-energy multifunctional active water is mainly in the form of vein instillation. Its mechanism of action is generally by a single stable water molecule directly acting on different areas in human body via the blood circulation of human body and directly entering the cells in the areas. Therefore, the particle-energy multifunctional active water activates the cells in the nervous system, promotes the metabolic function that was damaged of the cells, stimulates the self-metabolism ability of nerve cells, repairs irreversible brain cell trauma, and restores the brain areas that were damaged by drug addiction to normal functions, thereby realizing the rehabilitation treatment.

The major clinical manifestation is that the water can repair the receptors and neurotransmitters of the midbrain-margin dopamine system (such as nucleus accumbens, hippocampus, perfrontal cortex, ventral tegmental area, and amygdaloid nucleus). The symptom of the changing of the reward system of brain that is formed by drug addiction is mitigated, which is the aim of rehabilitation that is realized by restoring the addiction brain function that is caused by exogenous drug dependence under the reward mechanism.

The clinical manifestation of the vein instillation by the particle-energy multifunctional water is the recovery of the dopamine nerve damage of the drug addicts caused by long-term drug addiction, which enables the drug addicts to achieve normal brain reward mechanism, recovers the quantity of dopamine required to generate excitement sense and joviality sense to the normal range, and reduces the dopamine tolerance that is caused by long term drug addiction. Additionally, after drug taking, the dopamine accumulation at the postsynaptic membrane appears to be removed, which obviously mitigates the excitement sense symptom that the brain function exceeds the normal range due to drug taking.

As for withdrawal symptoms, the dopamine system under the effect of the particle-energy multifunctional active water achieves the recovery of function degeneration, and the enhancing of transduction activities of the midbrain dopamine and 5-hydroxytryptamine, thereby mitigating the disgusting and anxiety phenomena that the drug abstainers show in the withdrawal stage.

On the basis of the current observation on the clinical manifestation of applying the particle-energy multifunctional active water on rehabilitation, the withdrawal symptoms and drug dependence symptoms that are generated in conventional medicine treatments have not emerged. Additionally, the water has the effect of repairing the brain injuries caused by drug addiction, and the damaged space perception function and the audition of the drug addicts have been recovered to a certain extent.

5. The Application of the Particle-Energy Multifunctional Active Water in Agriculture The particle-energy multifunctional active water does not only excellently promote the propagation of animal cells, but also has obvious effects on plant cells. The rapeseeds that have been soaked by the particle-energy multifunctional active water do not only have fast growth after planting, but also have bigger heights of the grown rapes than those of the unsoaked seeds, by approximately one time. By slicing a potato and soaking by 12 hours, it can grow to about 350 mm only 13 days after the seeding and budding. By spraying flowers by using the particle-energy multifunctional active water, the flowering season can be prolonged by above one time.

EXAMPLE 2

The raw materials and the proportions thereof of the composite material for preparing particle-energy multifunctional active water of this Example are as follows:

a. Silicon nanometer-sized particles, as the base of the composition of the composite material, whose mass accounts for 21.03% of the composition of the composite material;

b. Rhenium nanometer-sized particles, whose mass accounts for 10.37% of the composition of the composite material;

c. Platinum nanometer-sized particles, whose mass accounts for 29.05% of the composition of the composite material;

d. Germanium nanometer-sized particles with the purity of 97%, whose mass accounts for 10.15% of the composition of the composite material;

e. Niobium nanometer-sized particles, whose mass accounts for 14.45% of the composition of the composite material;

f. Nickel nanometer-sized particles, whose mass accounts for 9.05% of the composition of the composite material;

g. Selenium nanometer-sized particles, whose mass accounts for 4.87% of the composition of the composite material; and h. Magnesium nanometer-sized particles, whose mass accounts for 1.03% of the composition of the composite material.

(II) The method for preparing the composite material of this Example:

Mixing the above nanometer-sized particles of silicon, rhenium, platinum, germanium, niobium, nickel, selenium and magnesium under vacuum; after the material mixing, conducting particle-energy magnetization in a magnetizer, wherein in the magnetization process the magnetization intensity should reach 10 A/m, and the magnetization intensity is maintained for 150 h; after the magnetization performing sintering by conversion between a lower temperature and a higher temperature, by placing the material in a forming mould, and firstly sintering at 850° C. for 2.1 h, and then sintering at the constant temperature of 950° C. for 12 h; and after the sintering, conducting magnetization again, wherein the magnetization intensity is 95 A/m, and the magnetization is conducted at the normal temperature continuously for 245.1 h.

(III) The method for preparing particle-energy multifunctional active water by using the composite material in a device of this Example is the same as that of Example 1.

(IV) The detection and verification of the properties of the particle-energy multifunctional active water that is prepared in this Example:

A. Regarding the Structure of the Water Molecules:

Under transmission electron microscopy, the structure of the particle-energy multifunctional active water of this Example presents the appearance of randomly arranged small molecule groups, whose diameters are below 1 nm, which is smaller than those of conventional small molecule group water (large molecule group water refers to the water molecule group that is formed by the aggregation of more than 10 water molecules, and its diameter is greater than 2.6 nm; and small molecule group water refers to the water molecule group that is formed by the aggregation of 5-7 water molecules, and its diameter is 1.1-1.6 nm). Under scanning tunneling microscope, the molecules of the particle-energy multifunctional active water are arranged by single water molecules. Note: the resolution of the transmission electron microscopy (ST) is one millionth of a millimeter, and the resolution of the scanning tunneling microscope (STM) is 1 part per hundred million of a millimeter.

B. Regarding the Examination on the Water Quality of the Particle-Energy Multifunctional Active Water:

The results of the detection by National Institute of Environmental Health, Chinese Center for Disease Control and Prevention can be seen in the following table:

Physical and Chemical Indicators

| Serial No. | Detection Item | Unit | Requirement by National Standards | Detection Result | Item Conclusion |
|---|---|---|---|---|---|
| 1 | Chromaticity | Degree | ≤15 | <5 | Qualified |
| 2 | Turbidity | NTU | ≤1 | 0.43 | Qualified |
| 3 | Odor and Smell | Description | Should Not Exist | None | Qualified |
| 4 | Material Visible by Bare Eye | Description | Should Not Exist | None | Qualified |
| 5 | pH | / | 6.5-8.5 | 6.64 | Qualified |
| 6 | Total Hardness (Counted in Calcium Carbonate) | mg/L | ≤450 | 14 | Qualified |
| 7 | Aluminum | mg/L | ≤0.2 | <0.002 | Qualified |
| 8 | Iron | mg/L | ≤0.3 | <0.0003 | Qualified |
| 9 | Manganese | mg/L | ≤0.1 | <0.0001 | Qualified |
| 10 | Copper | mg/L | ≤1 | <0.0001 | Qualified |
| 11 | Zinc | mg/L | ≤1 | <0.0001 | Qualified |
| 12 | Sulfate | mg/L | ≤250 | 14.3 | Qualified |

-continued

| Serial No. | Detection Item | Unit | Requirement by National Standards | Detection Result | Item Conclusion |
|---|---|---|---|---|---|
| 13 | Chloride | mg/L | ≤250 | 7.95 | Qualified |
| 14 | Total Dissolved Solids | mg/L | ≤1000 | 58 | Qualified |
| 15 | Oxygen Consumption | mg/L | ≤3 | 1.14 | Qualified |
| 16 | Volatile Phenols | mg/L | ≤0.002 | <0.002 | Qualified |
| 17 | Anionic Synthetic Detergent | mg/L | ≤0.3 | <0.05 | Qualified |
| 18 | Cyanide | mg/L | ≤0.05 | <0.002 | Qualified |
| 19 | Fluoride | mg/L | ≤1.0 | 0.18 | Qualified |
| 20 | Arsenic | mg/L | ≤0.01 | <0.0005 | Qualified |
| 21 | Selenium | mg/L | ≤0.01 | <0.0001 | Qualified |
| 22 | Mercury | mg/L | ≤0.001 | <0.00001 | Qualified |
| 23 | Cadmium | mg/L | ≤0.005 | <0.00005 | Qualified |
| 24 | Chromium (+6) | mg/L | ≤0.05 | <0.004 | Qualified |
| 25 | Nitrate Nitrogen | mg/L | ≤10 | 1.99 | Qualified |
| 26 | Lead | mg/L | ≤0.01 | <0.0001 | Qualified |
| 27 | Trichloromethane | mg/L | ≤60 | <0.5 | Qualified |
| 28 | Carbon Tetrachloride | mg/L | ≤2 | <0.1 | Qualified |

It can be seen in the above table that, the contents of the minerals and ions in the particle-energy multifunctional active water are far below the national standards, and the water substantially belongs to the scope of pure water.

Microorganism Indicators

| Detection Item | Detection Result | Stand Limit Value |
|---|---|---|
| Total Bacterial Count (CFU/mL) | 0 | 100 |
| Total Escherichia Coli (MPN/100 mL) | Undetected | Not Detectable |
| Escherichia Coli (MPN/100 mL) | Undetected | Not Detectable |

C. Regarding the Density of the Particle-Energy Multifunctional Active Water

The detection method: accurately measuring 1 m³ of the particle-energy multifunctional active water, and weighing.

By the detection, it is found that at the normal temperature, the density is 1.002-1.004 g/cm³, and the water is so far the only water whose density exceeds 1 g/cm³ (the density of the ordinary water at the normal temperature is 0.998 g/cm³).

E. Stability

Even heating the particle-energy multifunctional active water that is prepared in this Example to 100° C. cannot change the functional characteristics and activity of the particle-energy multifunctional active water, and cannot cause the particle-energy multifunctional active water to be associated and reduced into the normal water. After standing for 3 years, by verifying by activity experimentation, its activity does not have any deterioration.

F. Activity

The properties of the particle-energy multifunctional active water of this Example are not changed after long-term storage:

a. The particle-energy multifunctional active water that is prepared in this Example are placed into a glass, plastic or aluminum container and sealed (500 g container), and beer, white spirit or cigarette closely adheres to the wall of the container. After two hours, the tastes of the wines and the cigarette obviously change, and their mouthfeels are obviously improved. The particle-energy multifunctional active water can penetrate the container to act on other objects, and its energy effect principle and energy source are not clearly known so far.

b. The particle-energy multifunctional active water is placed into a water bed that is made from a polymer material, and after a person lies on it for 30-45 minutes, his fatigue completely disappears. A patient of cervical spondylosis simply places a plastic bottle of the particle-energy multifunctional active water under the neck before sleeping, and after 4-5 hours the pain sense significantly alleviates or even disappears.

G. Nuclear Magnetic Resonance

The nuclear magnetic resonance is performed at 48-50 Hz.

(V) The applications of the particle-energy multifunctional active water that is prepared in this Example The methods for treating cancers, hypertension, hypotension, allergy, cardiac extra systole and so on and the methods for daily healthcare by applying the particle-energy multifunctional active water that is prepared in this Example are the same as those of Example 1, and the applications obtain the same effects of mitigation and treatment as those of Example 1.

EXAMPLE 3

The raw materials and the proportions thereof of the composite material for preparing particle-energy multifunctional active water of this Example are as follows:

a. Silicon nanometer-sized particles, as the base of the composition of the composite material, whose mass accounts for 36.89% of the composition of the composite material;

b. Rhenium nanometer-sized particles, whose mass accounts for 25.37% of the composition of the composite material;

c. Platinum nanometer-sized particles, whose mass accounts for 8.48% of the composition of the composite material;

d. Germanium nanometer-sized particles with the purity of 97%, whose mass accounts for 18.10% of the composition of the composite material;

e. Niobium nanometer-sized particles, whose mass accounts for 5.05% of the composition of the composite material;

f. Nickel nanometer-sized particles, whose mass accounts for 1.16% of the composition of the composite material;

g. Selenium nanometer-sized particles, whose mass accounts for 1.12% of the composition of the composite material; and h. Magnesium nanometer-sized particles, whose mass accounts for 3.83% of the composition of the composite material.

(II) The method for preparing the composite material of this Example:

Mixing the above nanometer-sized particles of silicon, rhenium, platinum, germanium, niobium, nickel, selenium and magnesium under vacuum; after the material mixing, conducting particle-energy magnetization in a magnetizer, wherein in the magnetization process the magnetization intensity should reach 10 A/m, and the magnetization intensity is maintained for 150 h; after the magnetization performing sintering by conversion between a lower temperature and a higher temperature, by placing the material in a forming mould, and firstly sintering at 850° C. for 2.1 h, and then sintering at the constant temperature of 950° C. for 12 h; and after the sintering, conducting magnetization again, wherein the magnetization intensity is 95 A/m, and the magnetization is conducted at the normal temperature continuously for 245.1 h.

(III) The method for preparing particle-energy multifunctional active water by using the composite material in a device of this Example is the same as that of Example 1.

(IV) The detection and verification of the properties of the particle-energy multifunctional active water that is prepared in this Example:

A. Regarding the Structure of the Water Molecules:

Under transmission electron microscopy, the structure of the particle-energy multifunctional active water of this Example presents the appearance of randomly arranged small molecule groups, whose diameters are below 1 nm, which is smaller than those of conventional small molecule group water (large molecule group water refers to the water molecule group that is formed by the aggregation of more than 10 water molecules, and its diameter is greater than 2.6 nm; and small molecule group water refers to the water molecule group that is formed by the aggregation of 5-7 water molecules, and its diameter is 1.1-1.6 nm). Under scanning tunneling microscope, the molecules of the particle-energy multifunctional active water are arranged by single water molecules. Note: the resolution of the transmission electron microscopy (ST) is one millionth of a millimeter, and the resolution of the scanning tunneling microscope (STM) is 1 part per hundred million of a millimeter.

B. Regarding the Examination on the Water Quality of the Particle-Energy Multifunctional Active Water:

The results of the detection by National Institute of Environmental Health, Chinese Center for Disease Control and Prevention can be seen in the following Table 1 and Table 2:

The results of the detection by National Institute of Environmental Health, Chinese Center for Disease Control and Prevention can be seen in the following table:

Physical and Chemical Indicators

| Serial No. | Detection Item | Unit | Requirement by National Standards | Detection Result | Item Conclusion |
|---|---|---|---|---|---|
| 1 | Chromaticity | Degree | ≤15 | <5 | Qualified |
| 2 | Turbidity | NTU | ≤1 | 0.41 | Qualified |
| 3 | Odor and Smell | Description | Should Not Exist | None | Qualified |
| 4 | Material Visible by Bare Eye | Description | Should Not Exist | None | Qualified |
| 5 | pH | / | 6.5-8.5 | 7.03 | Qualified |
| 6 | Total Hardness (Counted in Calcium Carbonate) | mg/L | ≤450 | 11 | Qualified |
| 7 | Aluminum | mg/L | ≤0.2 | <0.002 | Qualified |
| 8 | Iron | mg/L | ≤0.3 | <0.0003 | Qualified |
| 9 | Manganese | mg/L | ≤0.1 | <0.0001 | Qualified |
| 10 | Copper | mg/L | ≤1 | <0.0001 | Qualified |
| 11 | Zinc | mg/L | ≤1 | <0.0001 | Qualified |
| 12 | Sulfate | mg/L | ≤250 | 15.1 | Qualified |
| 13 | Chloride | mg/L | ≤250 | 8.01 | Qualified |
| 14 | Total Dissolved Solids | mg/L | ≤1000 | 63 | Qualified |
| 15 | Oxygen Consumption | mg/L | ≤3 | 1.18 | Qualified |
| 16 | Volatile Phenols | mg/L | ≤0.002 | <0.002 | Qualified |
| 17 | Anionic Synthetic Detergent | mg/L | ≤0.3 | <0.05 | Qualified |
| 18 | Cyanide | mg/L | ≤0.05 | <0.002 | Qualified |
| 19 | Fluoride | mg/L | ≤1.0 | 0.25 | Qualified |
| 20 | Arsenic | mg/L | ≤0.01 | <0.0005 | Qualified |
| 21 | Selenium | mg/L | ≤0.01 | <0.0001 | Qualified |
| 22 | Mercury | mg/L | ≤0.001 | <0.00001 | Qualified |
| 23 | Cadmium | mg/L | ≤0.005 | <0.00005 | Qualified |
| 24 | Chromium (+6) | mg/L | ≤0.05 | <0.004 | Qualified |
| 25 | Nitrate Nitrogen | mg/L | ≤10 | 1.88 | Qualified |
| 26 | Lead | mg/L | ≤0.01 | <0.0001 | Qualified |
| 27 | Trichloromethane | mg/L | ≤60 | <0.5 | Qualified |
| 28 | Carbon Tetrachloride | mg/L | ≤2 | <0.1 | Qualified |

It can be seen in the above table that, the contents of the minerals and ions in the particle-energy multifunctional active water are far below the national standards, and the water substantially belongs to the scope of pure water.

Microorganism Indicators

| Detection Item | Detection Result | Stand Limit Value |
| --- | --- | --- |
| Total Bacterial Count (CFU/mL) | 0 | 100 |
| Total *Escherichia Coli* (MPN/100 mL) | Undetected | Not Detectable |
| *Escherichia Coli* (MPN/100 mL) | Undetected | Not Detectable |

C. Regarding the Density of the Particle-Energy Multifunctional Active Water

The detection method: accurately measuring 1 m$^3$ of the particle-energy multifunctional active water, and weighing.

By the detection, it is found that at the normal temperature, the density is 1.002-1.004 g/cm$^3$, and the water is so far the only water whose density exceeds 1 g/cm$^3$ (the density of the ordinary water at the normal temperature is 0.998 g/cm$^3$).

E. Stability

Even heating the particle-energy multifunctional active water that is prepared in this Example to 100° C. cannot change the functional characteristics and activity of the particle-energy multifunctional active water, and cannot cause the particle-energy multifunctional active water to be reduced into the normal water.

After standing for 3 years, by verifying by activity experimentation, its activity does not have any deterioration.

F. Activity

The properties of the particle-energy multifunctional active water of this Example are not changed after long-term storage:

a. The particle-energy multifunctional active water that is prepared in this Example are placed into a glass, plastic or aluminum container and sealed (500 g container), and beer, white spirit or cigarette closely adheres to the wall of the container. After two hours, the tastes of the wines and the cigarette obviously change, and their mouthfeels are obviously improved.

b. The particle-energy multifunctional active water is placed into a water bed that is made from a polymer material, and after a person lies on it for 30-45 minutes, his fatigue completely disappears. A patient of cervical spondylosis simply places a plastic bottle of the particle-energy multifunctional active water under the neck before sleeping, and after 2 hours the pain sense significantly alleviates or even disappears.

G. Nuclear Magnetic Resonance

The nuclear magnetic resonance is performed at 48-50 Hz.

(V) The applications of the particle-energy multifunctional active water that is prepared in this Example The methods for treating cancers, hypertension, hypotension, allergy, cardiac extra systole and so on and the methods for daily healthcare by applying the particle-energy multifunctional active water that is prepared in this Example are the same as those of Example 1, and the applications obtain the same effects of mitigation and treatment as those of Example 1.

The above examples are merely preferred examples that are presented to fully illustrate the present invention, and the protection scope of the present invention is not limited thereto. The equivalent substitutions or alternations that are made by a person skilled in the art on the basis of the present invention all fall within the protection scope of the present invention. The protection scope of the present invention is limited by the claims.

The invention claimed is:

1. A method for preparing a composite material, wherein the composite material comprises the following components: silicon, rhenium, platinum, germanium, niobium, nickel, selenium and magnesium, the method comprises the following steps:
   1) uniformly mixing silicon, rhenium, platinum, germanium, niobium, nickel, selenium and magnesium under vacuum;
   2) magnetizing the mixture that is obtained in the step 1) in a magnetizer, wherein a magnetization intensity is 5-10 A/m, and a magnetization duration is 100-200 h;
   3) placing the material that is magnetized in the step 2) in a forming mould, and conducting vacuum sintering; and
   4) magnetizing the material that is obtained in the step 3) in a magnetizer, wherein a magnetization intensity is 80-100 A/m, and a magnetization duration is 100-300 h, to obtain the composite material,
   wherein the silicon, rhenium, platinum, germanium, niobium, nickel, selenium and magnesium in the step 1) are all nanometer-sized particles, having an average length of 1-2 nm.

2. The method for preparing the composite material according to claim 1, wherein, the magnetization intensity in the step 2) is 7 A/m, and the magnetization duration is 120-125 h.

3. The method for preparing the composite material according to claim 1, wherein, a sintering temperature in the step 3) is 800-1000° C.

4. The method for preparing the composite material according to claim 1, wherein, the vacuum sintering in the step 3) is sintering by conversion between a lower temperature and a higher temperature, wherein the material that is magnetized in the step 1) is placed in the forming mould, and, under vacuum, is firstly sintered at a temperature of 800-850° C. for 1-3 h, and then sintered at a temperature of 900-1000° C. for 10-15 h.

5. The method for preparing the composite material according to claim 1, wherein, the magnetization intensity in the step 4) is 95-100 A/m, and a magnetization duration is 200-250 h.

\* \* \* \* \*